US008652162B2

(12) United States Patent
Morero

(10) Patent No.: US 8,652,162 B2
(45) Date of Patent: Feb. 18, 2014

(54) CATHETER, CATHETER ASSEMBLY AND RELEVANT METHOD

(75) Inventor: Massimo Morero, Roncadelle (IT)

(73) Assignee: Invatec S.p.A., Roncadelle (bs) (IT)

( * ) Notice: Subject to any disclaimer, the term of this patent is extended or adjusted under 35 U.S.C. 154(b) by 153 days.

(21) Appl. No.: 13/140,386

(22) PCT Filed: Dec. 18, 2008

(86) PCT No.: PCT/IT2008/000768
§ 371 (c)(1),
(2), (4) Date: Aug. 18, 2011

(87) PCT Pub. No.: WO2010/070684
PCT Pub. Date: Jun. 24, 2010

(65) Prior Publication Data
US 2011/0319903 A1 Dec. 29, 2011

(51) Int. Cl.
*A61M 29/00* (2006.01)
(52) U.S. Cl.
USPC .......................................................... 606/192
(58) Field of Classification Search
USPC .................. 606/192–194; 600/434, 585, 264;
604/101.01, 101.02, 96.01, 103.09,
604/524, 528; 623/1.35, 1.11–1.12
See application file for complete search history.

(56) References Cited

U.S. PATENT DOCUMENTS

| 5,275,611 | A | * | 1/1994 | Behl ............................. 606/198 |
| 5,605,543 | A | * | 2/1997 | Swanson ................... 604/102.02 |
| 5,702,439 | A | * | 12/1997 | Keith et al. ................. 604/96.01 |
| 5,833,706 | A | * | 11/1998 | St. Germain et al. ......... 606/194 |
| 5,868,700 | A | * | 2/1999 | Voda ............................. 604/510 |
| 5,879,499 | A | * | 3/1999 | Corvi ............................ 156/175 |
| 5,947,925 | A | * | 9/1999 | Ashiya et al. ............ 604/164.08 |
| 6,033,413 | A | * | 3/2000 | Mikus et al. ................... 606/108 |
| 6,379,365 | B1 | * | 4/2002 | Diaz ............................. 606/108 |
| 7,238,168 | B2 | * | 7/2007 | Sirhan et al. ............... 604/96.01 |
| 8,343,105 | B2 | * | 1/2013 | Windheuser et al. ..... 604/164.05 |
| 2001/0037085 | A1 | * | 11/2001 | Keith et al. ................. 604/96.01 |
| 2002/0123698 | A1 | | 9/2002 | Garibotto et al. |
| 2005/0209674 | A1 | * | 9/2005 | Kutscher et al. ............. 623/1.11 |
| 2008/0119693 | A1 | * | 5/2008 | Makower et al. ............. 600/114 |
| 2009/0171283 | A1 | * | 7/2009 | Schaeffer et al. ........ 604/103.08 |
| 2012/0150107 | A1 | * | 6/2012 | Cheung et al. ............. 604/96.01 |

FOREIGN PATENT DOCUMENTS

| EP | 0 796 633 | 9/1997 |
| WO | WO 97/76936 | 7/1997 |
| WO | WO 2007/089570 | 8/2007 |

* cited by examiner

Primary Examiner — Darwin Erezo
Assistant Examiner — Amy Shipley

(57) ABSTRACT

The present invention relates to a catheter suitable for conducting and positioning a medical device in an organic cavity comprising at least one side branch, such as a blood vessel, which comprises a tubular body, having a central lumen having a cross-section suitable for the passage of the medical device and a mandrel slidable in the central lumen and distally a flexible end portion. On the outer surface of the mandrel there is a longitudinal groove defining, with the inner wall of the tubular body, a passage suitable for receiving a first guide wire in a sliding manner. In addition, in the mandrel there is an inner lumen suitable for housing a second guide wire in a sliding manner. The present invention further relates to a catheter assembly comprising the aforesaid catheter and a method of use the same.

19 Claims, 12 Drawing Sheets

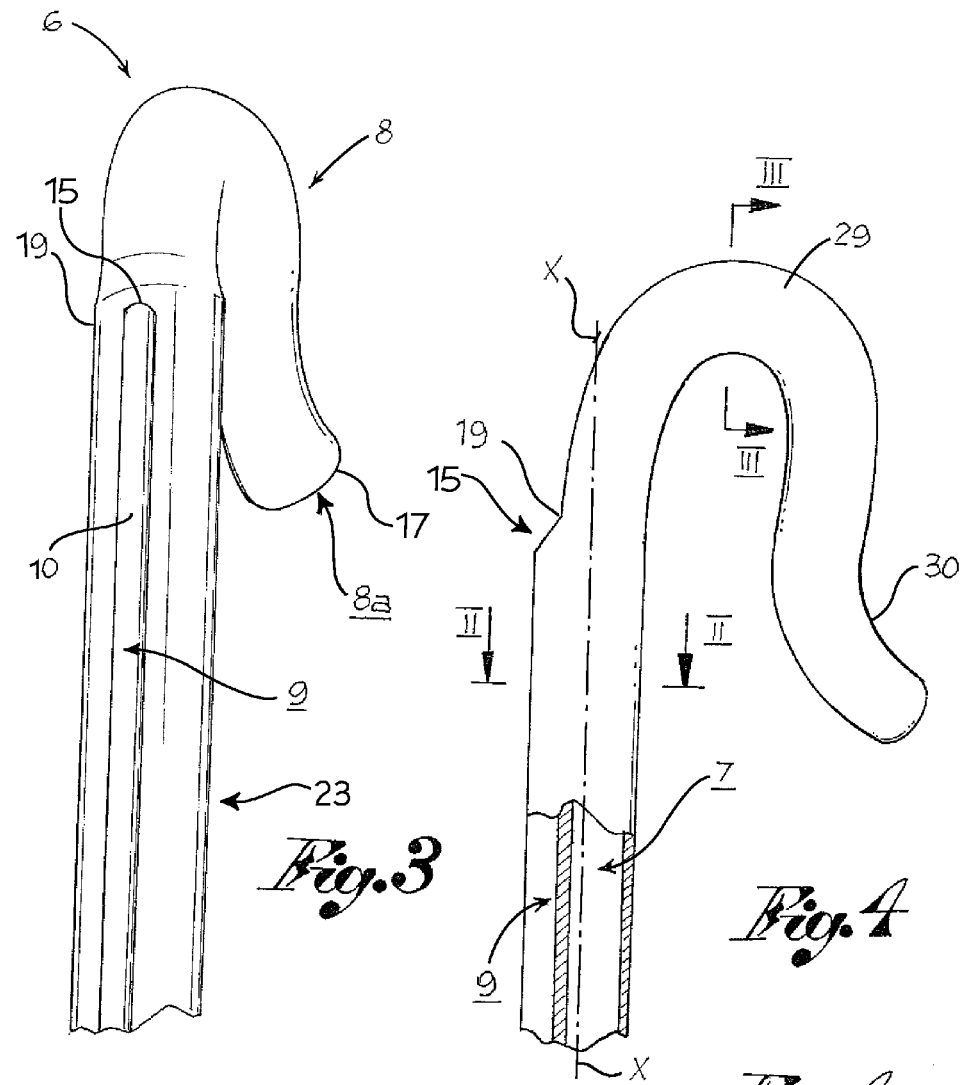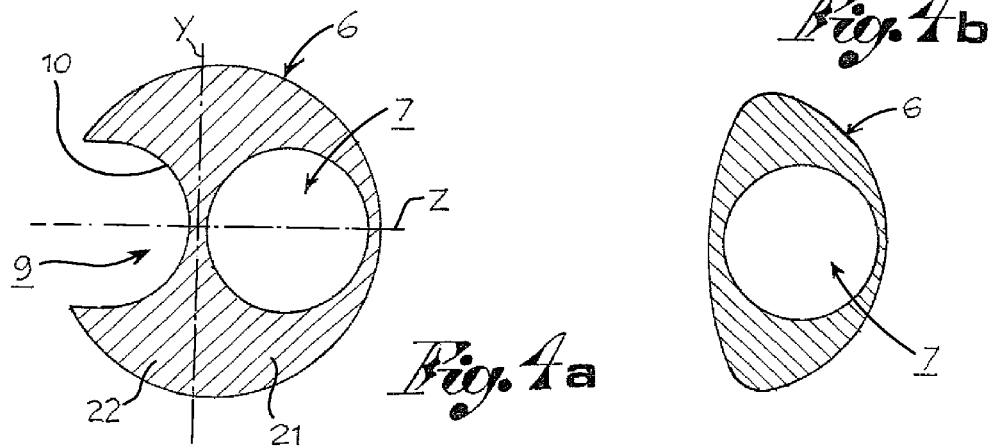

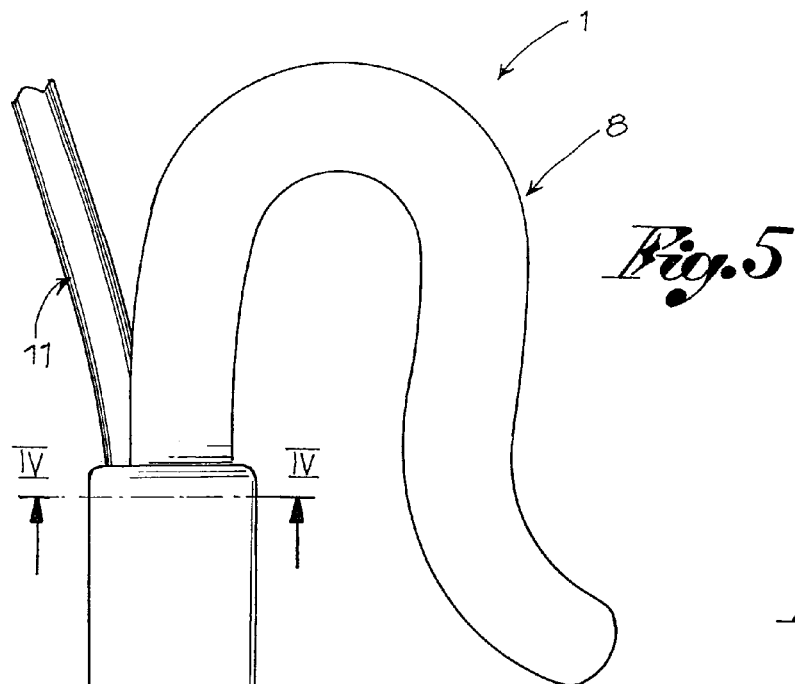
Fig.5
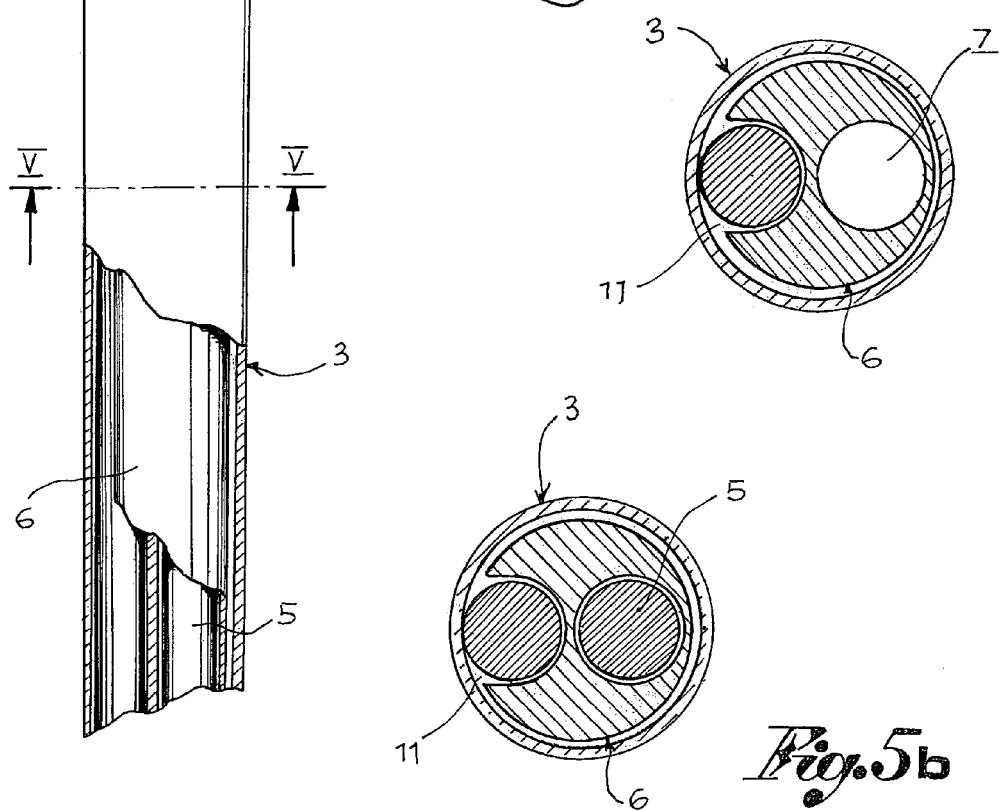
Fig.5a
Fig.5b

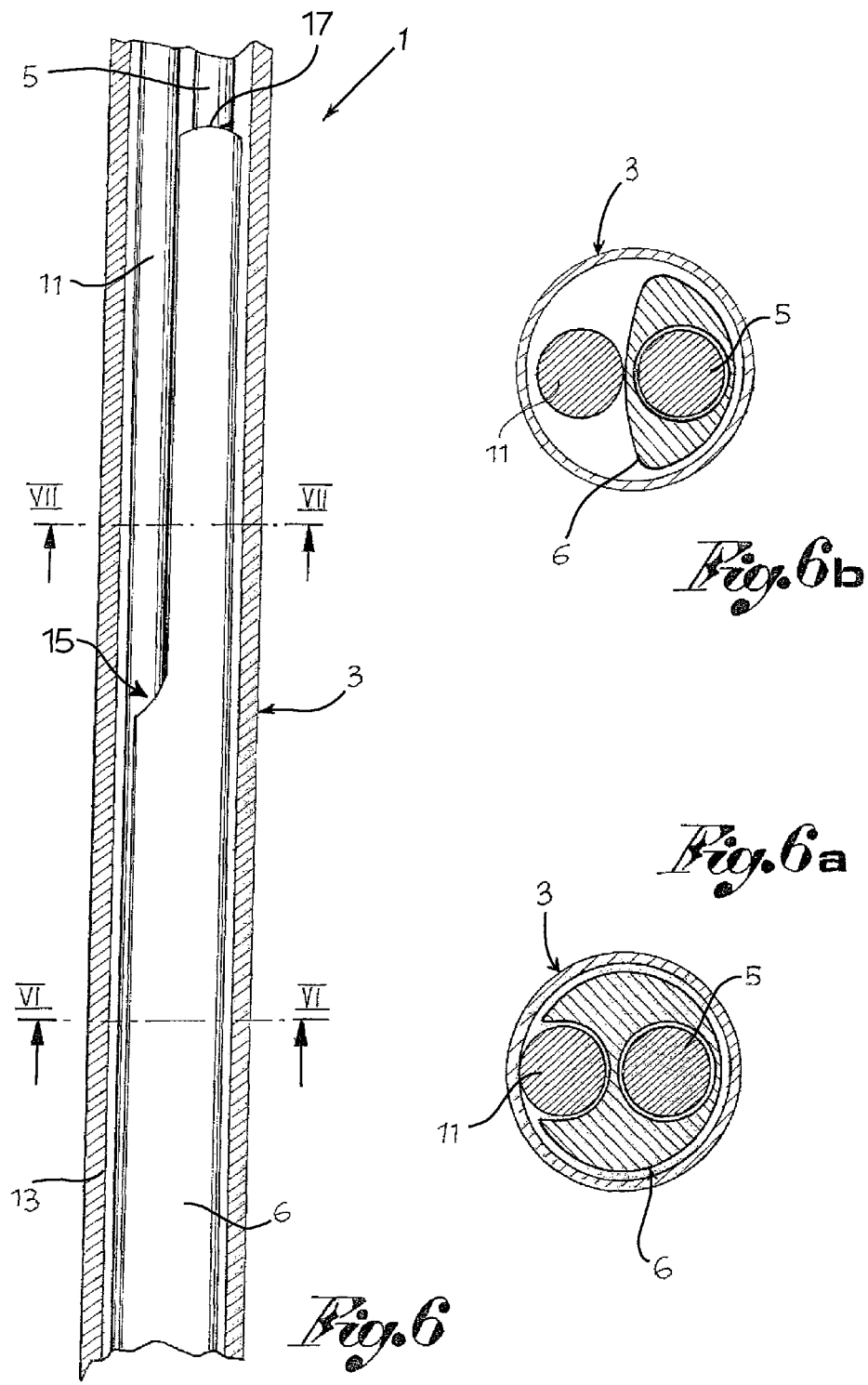

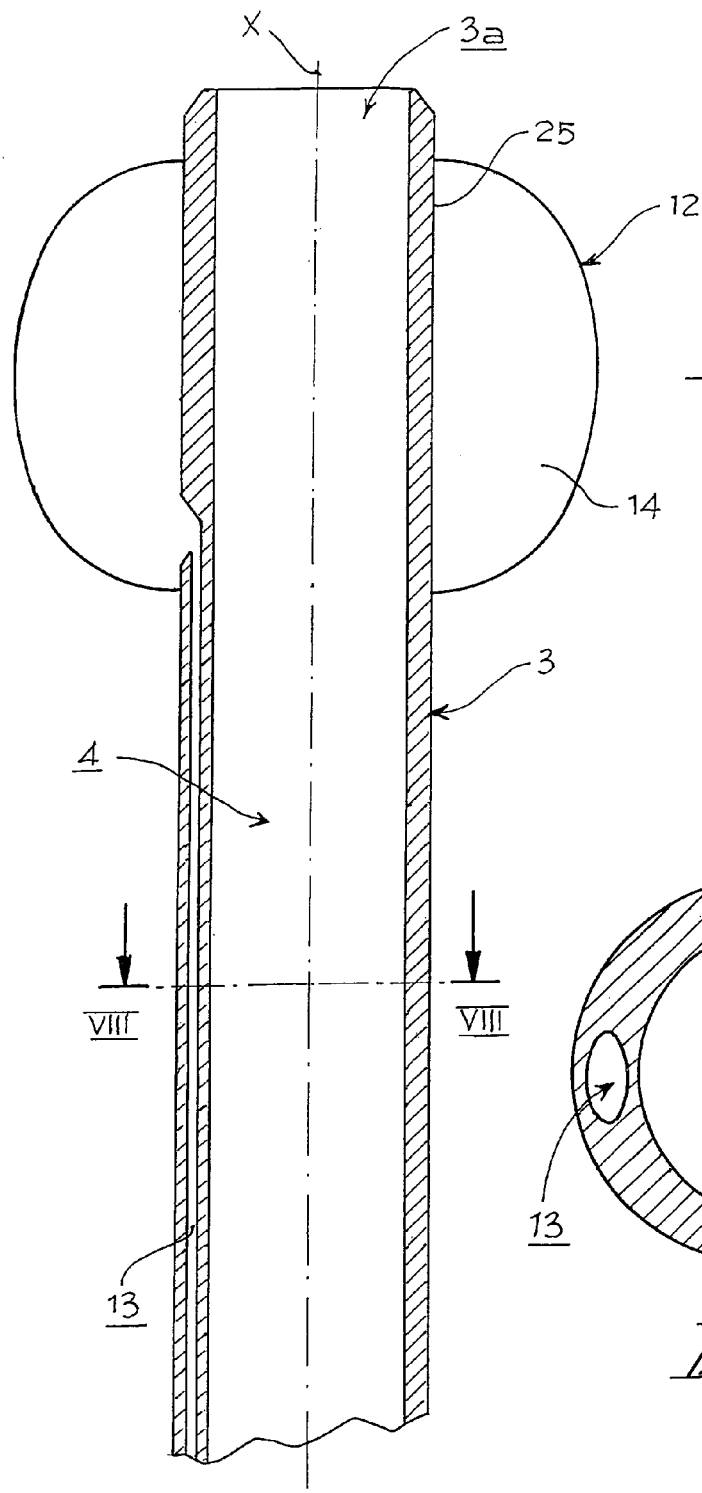
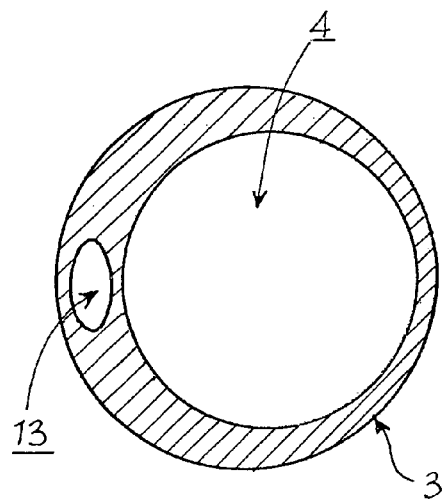
Fig.7
Fig.7a

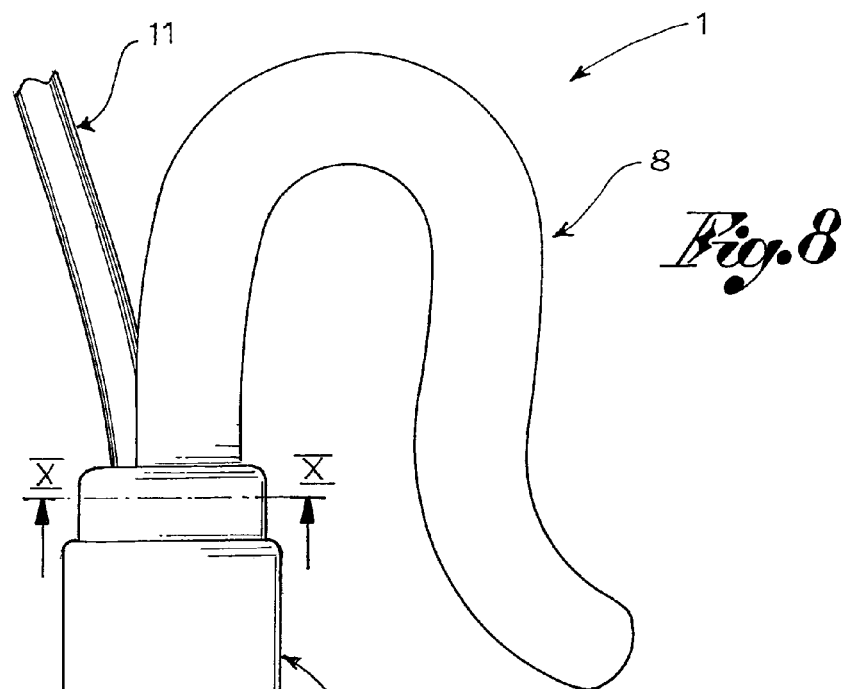
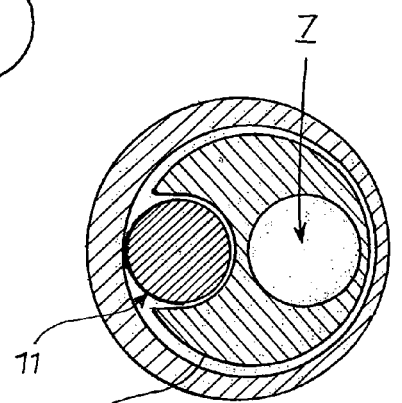
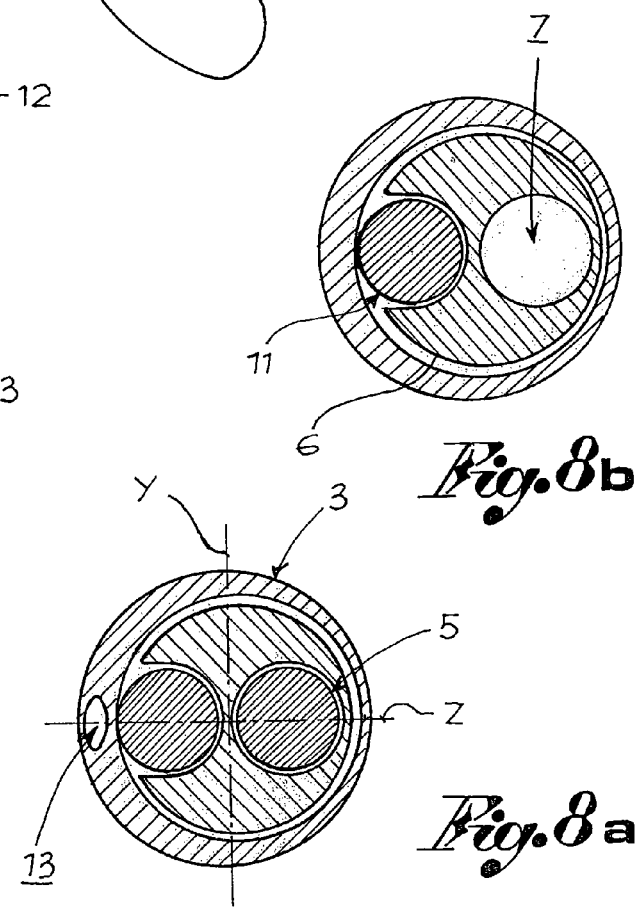
Fig. 8
Fig. 8b
Fig. 8a

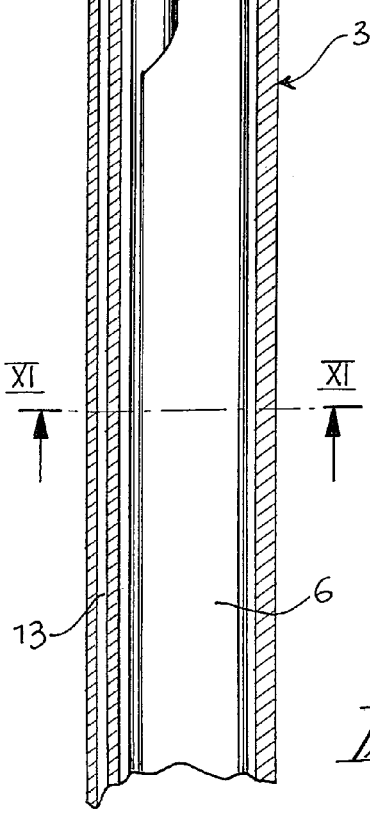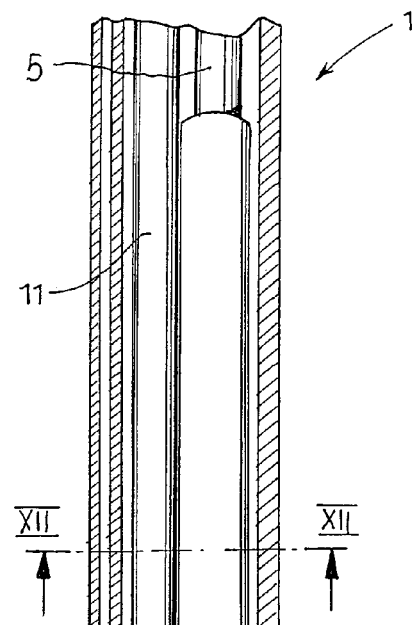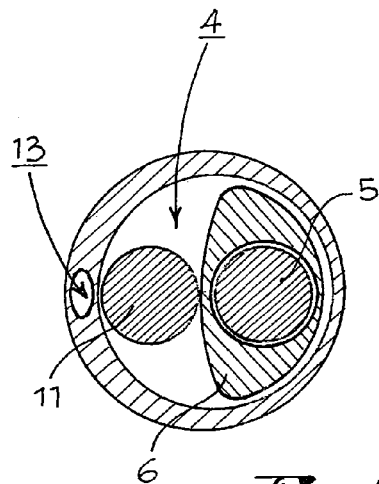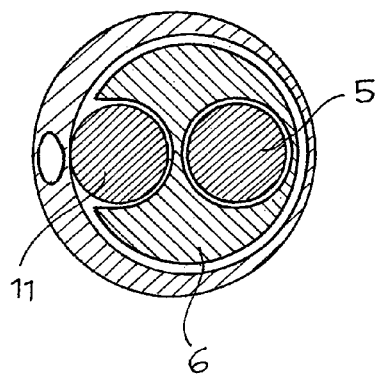
Fig. 9
Fig. 9a
Fig. 9b

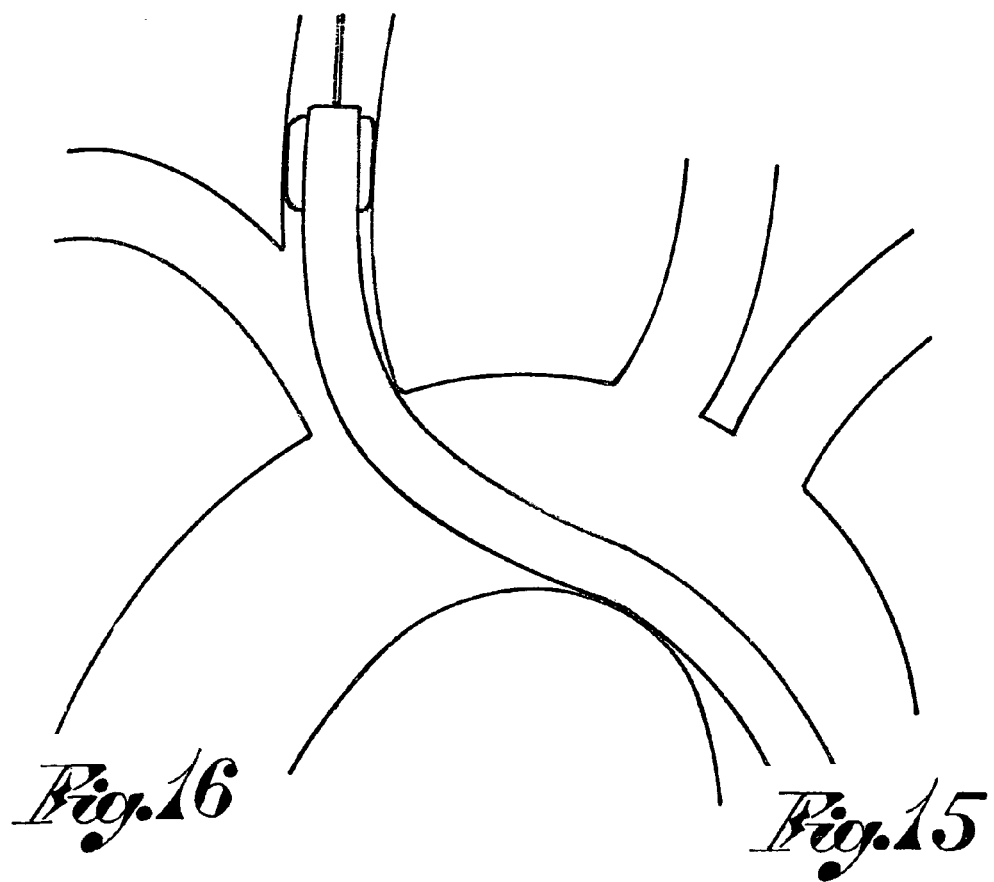
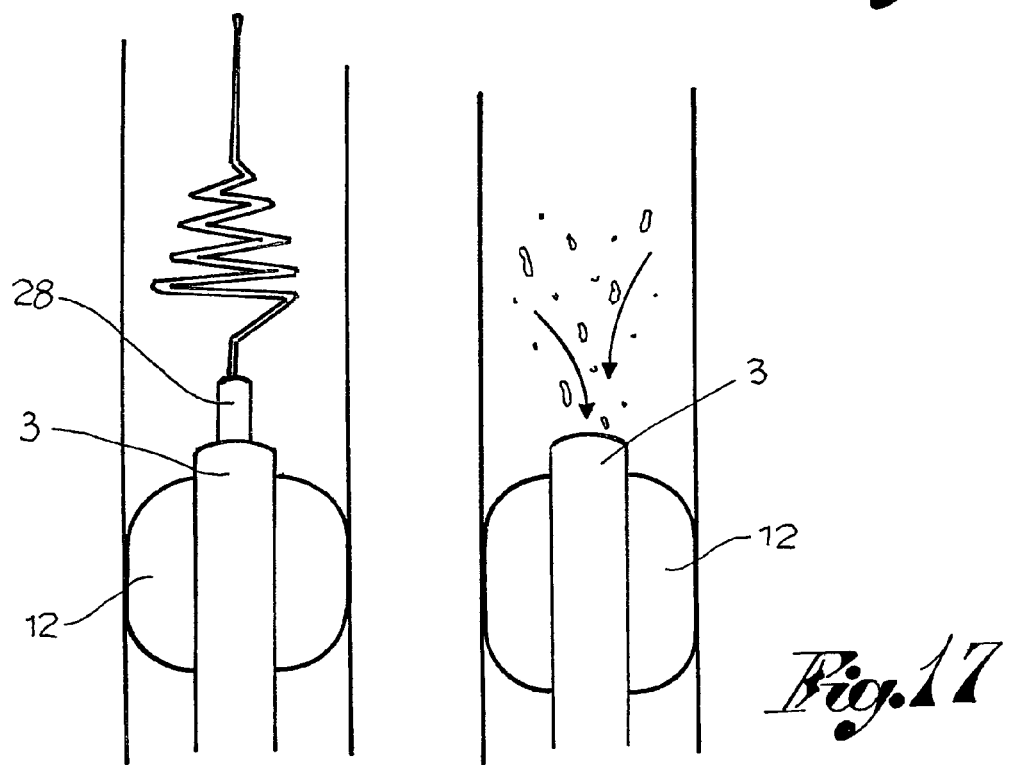

CATHETER, CATHETER ASSEMBLY AND RELEVANT METHOD

The present invention relates to a catheter, a catheter assembly and a method for conducting and positioning the latter inside an organic vessel. Specifically, the present invention relates to a device and a method for correctly and easily positioning a guide catheter inside a blood vessel difficult to reach due to its location and/or geometry.

A variety of catheters for conducting non-invasive operations inside a patient's organic cavities, for example inside blood vessels, are known of.

Depending on the position of the organic vessel of the patient being subjected to a non-invasive operation as above (for example an intravascular procedure), a guide wire may be introduced inside a blood vessel with or without the need to use further guiding means, such as for example a micro-catheter. In general; in the case of a supra-aortic application the guide wire is positioned without the help of a guide catheter, in other words without the use of any aid for the positioning and introduction of the guide wire. In the case of a peripheral application below the knee (BTK), however, the introduction of the guide wire is preferably performed with use of a micro-catheter. However, especially in the case in which the relevant vessel is hard to reach (for example in the presence of a bifurcation in which the side branch is substantially transversal to the main cavity), the operator (usually a physician) uses guiding devices which allow the directing and positioning of the guide wire in the correct position for performing the desired operation.

In this case, the operator generally uses a guide catheter inside which the guide is wire used to traverse the bifurcation and position itself inside the side branch. Once the bifurcation is reached, the guide catheter (in the cavity of which the guide wire is positioned) is rotated by the operator so as to align the tip of the guide catheter with the side branch to be engaged. Subsequently, once such alignment has been achieved, the operator pushes the guide wire along the inner cavity of the guide catheter, in the direction of and into the side branch.

Usually, a guide wire extends along a primary longitudinal axis and is fitted on the distal end with a flexible tip which can be shaped according to orientation requirements. Such tip extends along a secondary axis, incident to the primary.

The proximal portion of the guide wire is axially operable by the operator to advance along the organic vessel and rotate around the primary axis to control the orientation of the flexible tip. This way it is possible to lead the guide wire to where the intravascular procedure has to be performed.

Generally the guide wire (as such or inserted inside guiding means, such as a micro-catheter) is inserted into the patient's body (for example by means of an introducer) through an incision made in the femoral artery and conducted where needed to perform the intravascular procedure, for example in the aortic tract. Along the path, generally comprising a plurality of bifurcations and offshoots, the resilient tip has to be directed by the operator to make the guide wire follow the desired path.

Once the guide wire has reached the working position, a suitable catheter, for example a guide catheter or a device for performing an angioplasty operation, is fitted onto the proximal portion of the guide wire (outside the patient's body) and moved forward, up to the operation area, sliding coaxially along said guide wire.

However, when the operation area is difficult to reach, for example when the vessel being operated is the vessel or side branch of a bifurcation, the operator generally has to use more than one device to correctly position the guide wire and, later, the guide catheter or other medical device.

Document WO 2007/138638 describes a guide catheter fitted with a curved distal portion enabling the operator to position a guide wire in a vessel difficult to reach. In fact, the guide catheter described in the earlier document is used to intercept a bifurcation and position the guide wire in the side branch of the main vessel. However said guide catheter cannot also be subsequently used to allow a further medical device (for example another catheter) to be introduced into such side branch of the bifurcation. Consequently, in accordance with the guide catheter described by document WO 2007/138638, the operator must withdraw and retract the latter (used solely to position the guide wire) and move a further device forward along the already positioned guide wire which will be inserted in the side branch of the bifurcation.

Document U.S. Pat. No. 5,054,500 describes a catheter of the type which can be anchored comprising a central lumen, suitable for the passage of one or more medical devices, and a balloon, which when expanded, permits anchorage of the catheter to the inner walls of the blood vessel.

Document WO 03/002033 describes a release system of a medical device, said release system comprising a tubular element having a central lumen inside which a compact mandrel is inserted. Such mandrel comprises a lateral groove which defines, with the inner wall of the tubular element, a passage area for the insertion of a guide wire.

However, the devices described in documents U.S. Pat. No. 5,054,500 and WO 03/002033 cannot be used directly to position a guide wire inside a side branch difficult to reach, such as a side branch of a bifurcation.

Consequently, in the case in which the vessel to be treated is downstream of a bifurcation, the operator is obliged to first use a further device to correctly position the guide wire and, subsequently, to make a catheter of the type which can be anchored (described, for example, in document U.S. Pat. No. 5,054,500) or a release system (described, for example, in document WO 03/002033) slide along the now positioned guide wire.

To conclude, in all the cases described above, to reach the operation area and perform the desired intravascular procedure (for example an angioplasty operation), the operator must use more than one medical device. Specifically, the operator is obliged to use a first catheter to position the guide wire inside the side branch and a second catheter (inserted into the side branch by sliding it along the guide wire now in position) which acts as a guide catheter for the medical device which will be inserted to perform the desired operation.

This causes an inevitable increase in the time required to complete the operation desired, with a greater risk to the life of the patient, as well as an increased complexity of the procedure itself making the use of a greater number of medical devices necessary. Furthermore and not least, the use of a number of devices inevitably also affects the economic aspect increasing—in some cases to a considerable extent—the total cost of the entire procedure.

This way, furthermore, the potential risks to the patient increase, connected not just with the longer time of the operation but also with the danger of injury to the walls of the blood vessels and detachment of stenotic fragments as a result of rubbing against the walls of the relevant blood vessels by the steps of advancement and extraction of the numerous medical devices used.

The Applicant has perceived a need to design a single multipurpose device suitable for positioning a guide wire in a side branch of a bifurcation and also to surpass and advance inside such side branch and, if necessary, to anchor itself directly to the wall of the blood vessel where the operation, such as, an angioplasty or thromboaspiration has to be performed.

In a first aspect, the present invention therefore concerns a catheter suitable for conducting and positioning a medical device in an organic vessel comprising a main vessel and at least one side branch, said catheter comprising:

a tubular body having a central lumen extending along said tubular body around a longitudinal axis, said central lumen having a cross-section such as to allow the passage of at least one medical device;

a mandrel positioned in a sliding manner inside said central lumen, said mandrel distally comprising a flexible end portion, said catheter being characterised in that the mandrel further comprises:

an outer surface, facing the tubular body, having at least on the proximal portion a longitudinal groove, defining, with the inner wall of the tubular body, a passage suitable for receiving a first guide wire in a sliding manner, and an inner lumen suitable for receiving a second guide wire in a sliding manner.

In a further aspect, the present invention concerns a catheter assembly comprising:

a catheter as defined above;

a first guide wire, in relation to which the tubular body is axially slidable and suitable for turning said body around an axis substantially parallel to the longitudinal axis; and a second guide wire suitable for causing shape changes of the flexible end portion of the mandrel.

In a further aspect, the present invention concerns a medical apparatus comprising:

a catheter as defined above, and a further medical device engageable in a slidable manner in the central lumen of the tubular body of the catheter.

In a further aspect, the present invention concerns a method for conducting and positioning a medical device in an organic vessel comprising a main vessel and at least one side branch, said method comprising the steps of:

providing a catheter assembly as defined above;

introducing the tubular body into the main organic vessel;

introducing the mandrel into the tubular body;

moving the tubular body forward into the main organic vessel until its distal extremity is positioned in correspondence with the side branch;

moving the mandrel forward until its flexible end portion is positioned in correspondence with the side branch;

moving the second guide wire forward inside the side branch;

moving the catheter forward in the side branch.

The present invention will now be described in detail with the help of the attached figures, wherein:

FIG. 1a shows a cross-section performed along the line I-I of the catheter in FIG. 1;

FIG. 2 shows a lateral view in cross-section of a tubular body of the catheter which the present invention relates to;

FIGS. 3 and 4 respectively show a perspective view and a lateral view partially in cross-section of a mandrel of the catheter according to a possible embodiment of the present invention;

FIGS. 4a and 4b show two cross-sections of the mandrel in FIG. 4, taken respectively along the lines II-II and III-III thereof;

FIG. 5 shows a lateral view partially in cross-section of a catheter assembly according to the present invention;

FIGS. 5a and 5b show two cross-sections of the catheter in FIG. 5 respectively along the lines IV-IV and V-V;

FIG. 6 shows a lateral view partially in cross-section of the catheter according to the present invention, wherein the mandrel is positioned in a further possible configuration;

FIGS. 6a and 6b show two cross-sections of the catheter in FIG. 6, respectively along the lines VI-VI and VII-VII;

FIG. 7 shows a lateral view partially in cross-section of a tubular body of the catheter which the present invention relates to;

FIG. 7a shows a cross-section of the tubular body in FIG. 7, along the line VIII-VIII;

FIG. 8 shows a lateral view partially in cross-section of a catheter assembly according to a further variation of the present invention;

FIGS. 8a and 8b show two cross-sections of the catheter in FIG. 8, respectively along the lines IX-IX and X-X;

FIG. 9 shows a lateral view partially in cross-section of the catheter assembly according to a variation of the present invention, wherein the mandrel is positioned in a further possible configuration;

FIGS. 9a and 9b show two cross-sections of the catheter assembly of FIG. 9, respectively along the lines XI-XI and XII-XII;

FIGS. 10 to 17 show different steps of a functioning method of the catheter which the present invention relates to, according to a possible embodiment.

In the aforementioned figures reference number 1 globally indicates a catheter according to the present invention suitable for conducting and positioning a medical device (for example a guide wire, an angioplasty device, a thromboaspiration device or similar) into an organic vessel, such as for example a blood vessel. Specifically, the blood vessel comprises a main cavity 2 and at least one side branch 20. More specifically, the catheter according to the present invention proves particularly advantageous in the case in which the aforesaid side branch 20 is positioned in a direction substantially perpendicular to the longitudinal direction in which the main cavity 2 extends, said side branch defining a vessel substantially transversal to the longitudinal (axial) extension of the main cavity 2.

Figure 1:
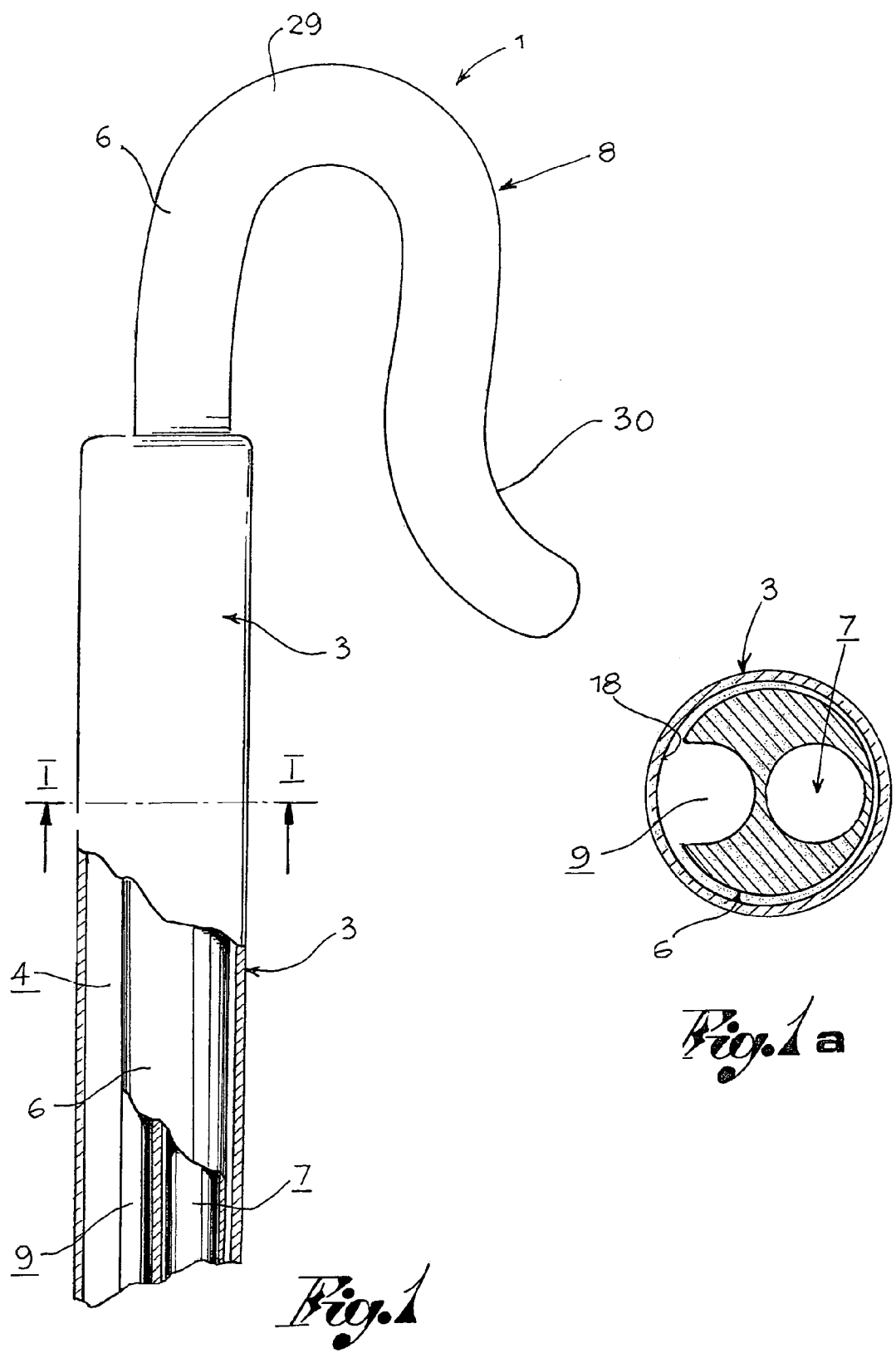
FIG. 1 shows a lateral view partially in cross-section of a catheter according to the present invention, wherein the mandrel is positioned according to a possible configuration thereof.
Figure 2:
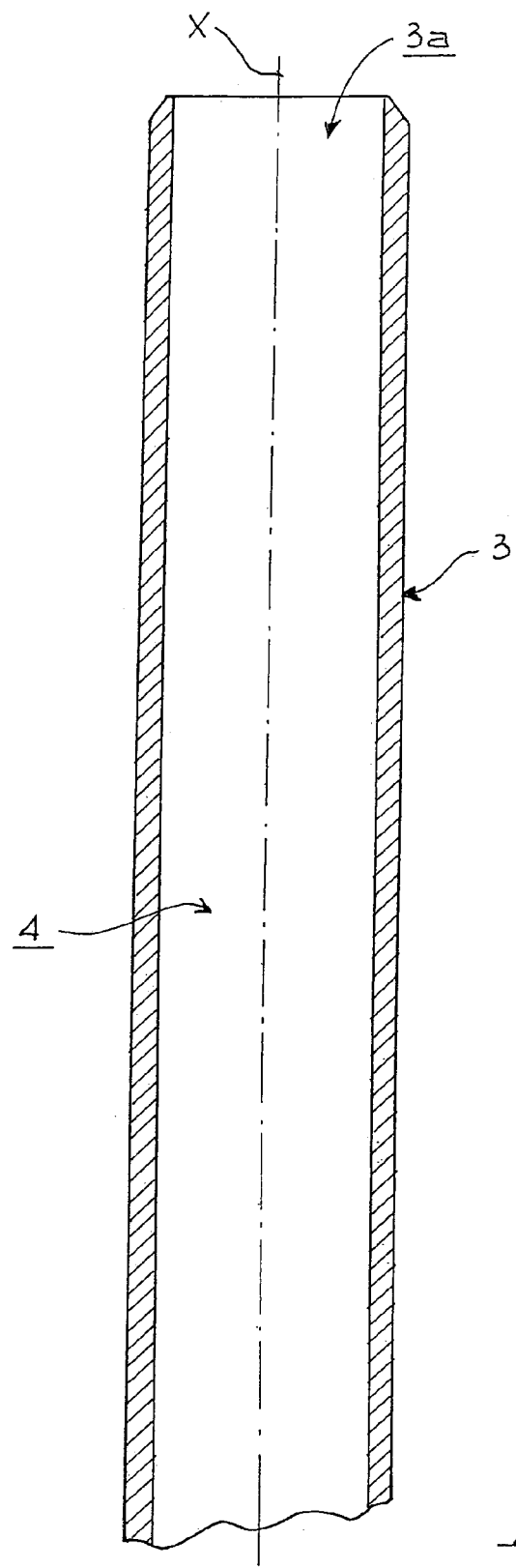

As shown in FIG. 1, the catheter 1 comprises a tubular body 3, having a central lumen 4 which extends along the entire longitudinal extension of the tubular body 3 around a longitudinal axis X (shown in FIG. 2). Such central lumen 4 has a cross-section suitable for the passage of at least one medical device.

In other words, the tubular body 3 identifies within it a central lumen 4 having a cross-section sufficient for housing in a slidable manner at least one medical device, said cross-section being defined intersecting the tubular body 3 with a plane substantially perpendicular to the longitudinal axis X.

The distal extremity of the tubular body 3 comprises an opening 3a (shown in FIG. 2) to allow accessing the central lumen 4.

Preferably, the cross-section of the opening 3a is equal to or greater than that of the central lumen 4. In FIG. 2 the dimensions of the cross-section of the opening 3a are equal to the dimensions of the cross-section of the central lumen 4.

The proximal extremity of the tubular body 3 (not shown in the figures) is usually joinable to a catheter connector, such as a one- or two-way connector.

The catheter 1 according to the present invention further comprises a mandrel 6 slidably positioned inside of the central lumen 4.

The mandrel 6 is therefore slidable, preferably axially, inside the central lumen 4 of the tubular body 3.

In other words, the mandrel 6 is suitable for being inserted inside the central lumen 4 of the tubular body 3 and for being moved longitudinally inside said lumen 4, that is in a direction substantially parallel to the longitudinal axis X.

As shown in FIGS. 3 and 4, the mandrel 6 distally comprises a flexible end portion 8 which, according to a preferred variation, is suitable for assuming a curved configuration in relation to the longitudinal axis X so as to intercept the side branch 20.

According to a preferred variation, the flexible end portion 8 is made of a flexible material, preferably a shape-memory material, which allows the tip of the mandrel 6 to convert from a rectilinear configuration (FIGS. 6 and 9), when inside it there is a more rigid guide element (such as a second guide wire 5), to a curved configuration (FIGS. 3 and 4), when the guide element is withdrawn or when a more flexible portion of such guide element is moved to the flexible end portion 8.

In the mandrel 6 there is an inner lumen 7, preferably with a circular cross-section (as shown in FIGS. 4a and 4b), suitable for receiving in a sliding manner a second guide wire 5 suitable for performing the shape changes of the flexible end portion 8 of the mandrel 6 as mentioned above.

Preferably, a distal extremity 17 of the flexible end portion 8 of the mandrel 6 comprises a tip opening 8a to allow access to the inner lumen 7 of the mandrel 6.

In other words, the inner lumen 7 of the mandrel 6 is accessible distally through the tip opening 8a.

In accordance with the present invention, the mandrel 6 also comprises an outer surface 10, facing the tubular body 3, provided (as shown, for example, in FIGS. 3 and 4a) at least on a proximal portion 23 with a longitudinal groove 9 defining, with an inner wall 18 of the tubular body 3, a passage suitable for receiving a first guide wire 11 in a sliding manner.

Consequently, when the mandrel 6 is positioned inside the lumen 4 of the tubular body 3, the outer surface 10 of the mandrel 6 identifies, with the inner wall 18 of the tubular body 3, a passage (shown, for example, in FIG. 1a) for a first guide wire 11 (shown, for example, in FIG. 5).

According to one embodiment of the present invention, the longitudinal groove 9 is substantially "U"-shaped (as shown in FIG. 4a).

According to a further embodiment of the present invention, the flexible end portion 8 of the mandrel 6 extends from the proximal extremity 19 to the distal extremity 17.

Preferably, the longitudinal groove 9 is made solely along the proximal extremity of the mandrel 6.

In other words, according to such embodiment, the longitudinal groove 9 extends along the entire rectilinear section of the mandrel 6 and ends at the proximal extremity 19 of the flexible end portion 8. This means that, in accordance with the aforementioned embodiment of the present invention, the flexible end portion 8 of the mandrel 6 lacks the longitudinal groove 9.

FIG. 4a shows the cross-section of the mandrel 6 along the line II-II of FIG. 4. Such cross-section is shown in detail in the plane Y-Z orthogonal to the longitudinal axis X. The Z axis passes substantially both through the centre of the inner lumen 7 of the mandrel 6, and through the centre of the longitudinal groove 9. The Y axis, orthogonal to the Z axis, passes at the solid portion of mandrel between the inner lumen 7 and the longitudinal groove 9. As a result, the Y axis separates the inner lumen 7 from the longitudinal groove and defines two portions of mandrel substantially semicircular: a first portion 21, in which the inner lumen 7 is made, and a second portion 22, in which the longitudinal groove 9 is made. The first portion 21 and the second portion 22 are axially adjacent and facing each other on their base side positioned along the Y axis.

Advantageously, the flexible end portion 8 of the mandrel 6 is the prolongation of the first, substantially semicircular portion 21 of the mandrel 6. This allows the longitudinal groove 9, made in the second, substantially semicircular, portion 22, to be distally opened in the direction of the longitudinal axis X, that is to present a distal opening 15 at the proximal extremity 19 of the flexible end portion 8. This way, the first guide wire 11 can protrude from the mandrel 6 parallel to the longitudinal axis X (as shown, for example, in FIG. 5), without having to perform unfavourable curves or direction deviations.

According to one embodiment of the present invention, the longitudinal groove 9 and the inner lumen of the mandrel 6 have respective longitudinal axes parallel to the longitudinal axis X.

According to a preferred embodiment, the longitudinal groove 9 and the inner lumen 7 of the mandrel 6 have respective longitudinal axes lying on a diameter of the mandrel, and specifically from opposite parts to the centre of the mandrel itself (origin of the axes Y and Z in FIG. 4a). Specifically, with reference to FIG. 4a, said longitudinal axes (not shown in the figure) intersect the Z axis. More specifically, said longitudinal axes intersect the Z axis from opposite sides in relation to the Y axis.

Preferably, the flexible end portion 8 is movable between a first configuration, wherein it extends substantially along the longitudinal axis X, and at least a second configuration, wherein it is curved.

Advantageously, in addition, the flexible end portion 8 is pre-shaped in such a way as to curve on the side opposite the longitudinal groove 9.

According to a particularly advantageous embodiment of the present invention, the flexible end portion 8 has a cross-section (on a plane perpendicular to the longitudinal axis X) of a flattened or squashed shape, for example, as shown in FIG. 4b that depicts the cross-section of the mandrel 6 along the line III-III of FIG. 4, the cross-section of the flexible end portion 8 has a substantially elliptical, oval or ovoid form.

Advantageously, the curvature of the flexible end portion 8 is performed around an axis parallel to the Y axis which identifies the main extension (greatest diameter) of the substantially semicircular cross-section 21. In other words, thanks to the flattened cross-section, the flexible end portion 8 bends (turns) in the direction of the Z axis, that side being the one that offers greater flexibility, or least resistance to the curvature (that is the least torsional rigidity).

Preferably, the flexible end portion 8 is pre-shaped so as to assume a substantially "U" shape.

Advantageously, thanks to the flattened shape and the pre-forming of the flexible end portion 8 of the mandrel 6, the operator can easily and rapidly identify the direction of curvature of said flexible end portion 8 and easily intercept the side branch of the bifurcation.

In other words, when the second guide wire 5 (which runs along the inner lumen 7 of the mandrel 6) is moved in a proximal direction, the flexible end portion 8 —thanks to its special configuration—proves advantageously directed towards the entrance of the side branch 20 to be engaged.

Alternatively, according to a further embodiment of the present invention, the flexible end portion 8 has a cross-section of a semi-circular shape.

According to a further embodiment (not shown in the figure) the catheter comprises an externally tapered portion in distal direction.

Preferably, the tapering affects two opposite lateral surfaces, symmetrical to a transversal axis Y.

Even more preferably, the tapering is substantially continuous all along the distal portion of the catheter, that is axially affecting the distal portion all along its longitudinal extension.

According to an alternative embodiment, the tapering is localised in a transition portion connecting the distal portion to the proximal portion 20 of said catheter.

In accordance with the embodiment of the present invention previously illustrated, the second guide wire 5 is movable and/or slidable in relation to the flexible end portion 8 between the first configuration, wherein the flexible end portion 8 extends substantially along the longitudinal axis X (FIGS. 6 and 10), and at least a second curved configuration, wherein the flexible end portion 8 is at least partially curved, as shown for example in FIG. 5.

Figure 10:
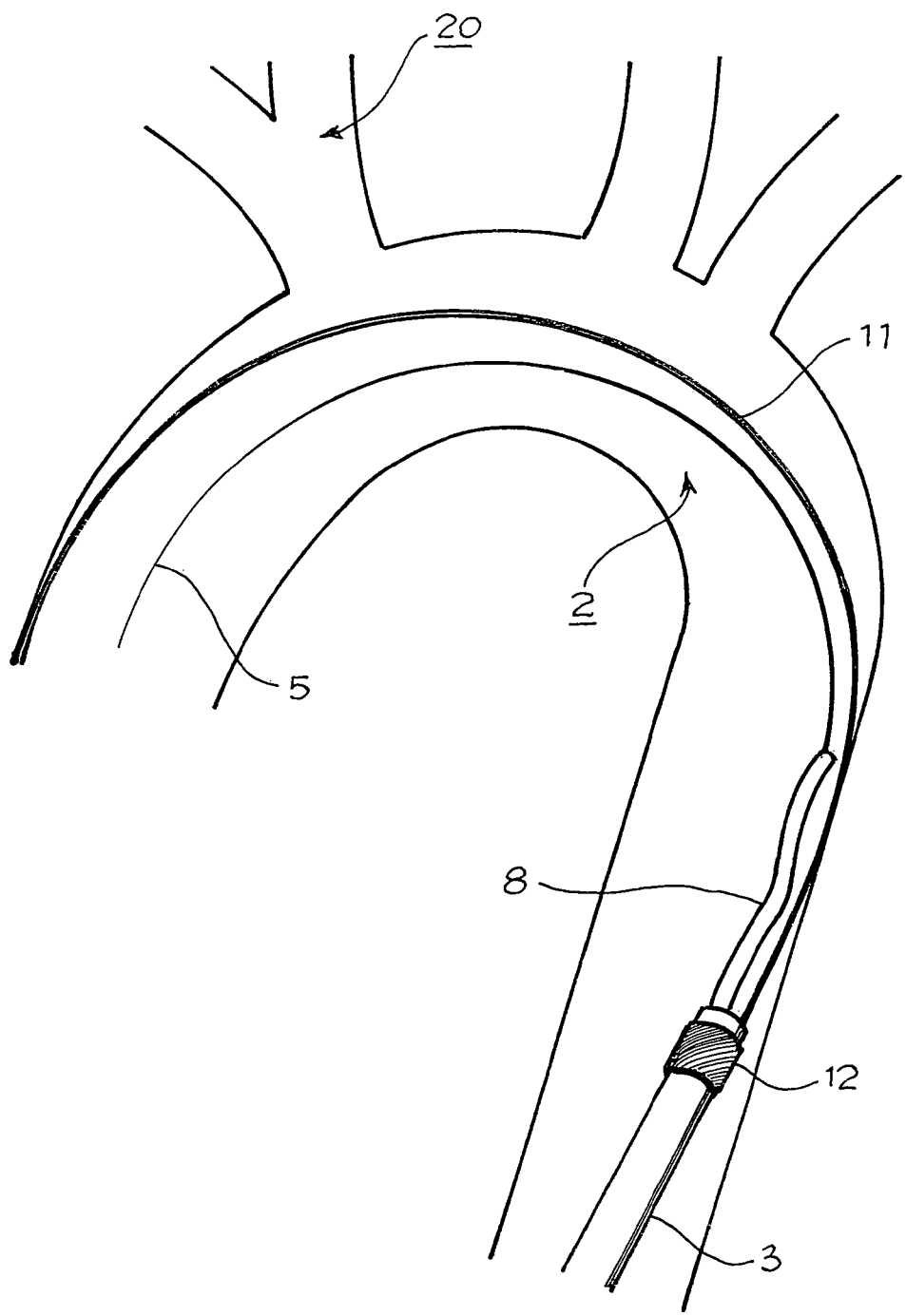

In other words, when the second guide wire 5 engages the inner lumen 7, as shown for example in FIG. 10, the second guide wire 5 acts as a support for the flexible end portion 8 so as to prevent the latter from assuming a curved shape and making it remain in the first, substantially rectilinear configuration.

Specifically, when the flexible end portion 8 is disposed in the first configuration, it substantially constitutes a longitudinal prolongation of the mandrel 6 along the longitudinal axis X and is particularly suitable for translating along a main cavity 2, as shown for example in FIG. 10.

When, however, the second guide wire 5 is retracted from the flexible end portion 8 leaving the latter unsupported, the flexible end portion can return to its curved shape, that is to the second configuration, as shown for example in FIG. 8.

Figure 12:
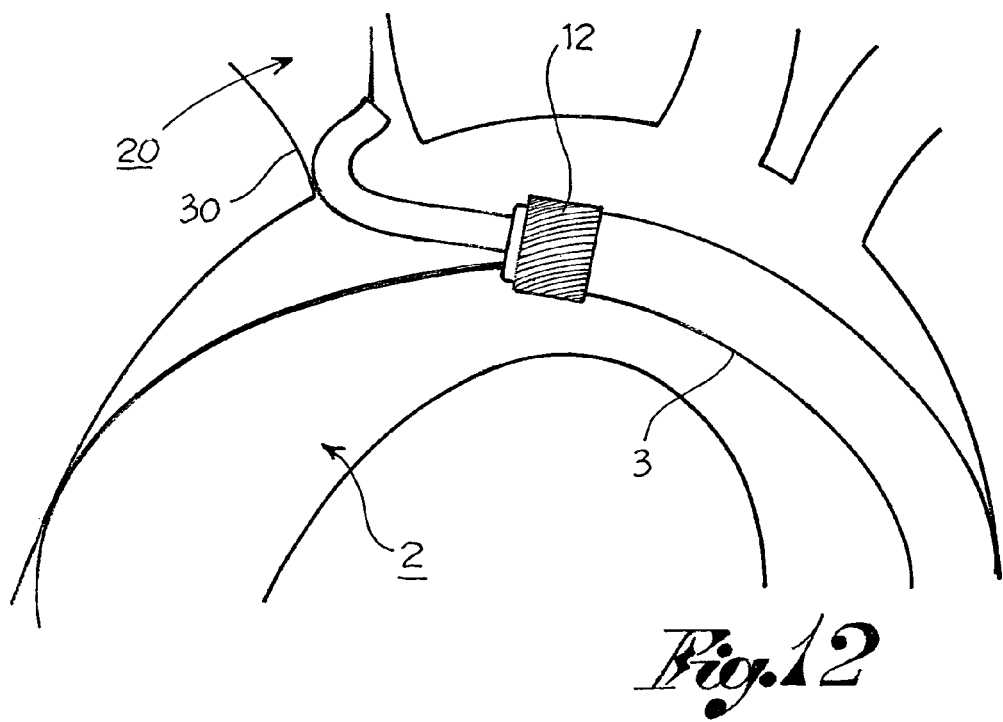

As a result, when the flexible end portion 8 assumes the second configuration, the aforesaid at least partial curvature, makes the flexible end portion 8 particularly suitable for engaging the side branch 20 extending from the main cavity 2, as shown in FIG. 12.

In other words, when passage of the catheter 1 inside a side branch 20 having a particularly accentuated inclination in relation to the main cavity 2 is required (for example in the case in which the side branch 20 breaks off the main cavity 2 in a direction substantially perpendicular to the latter), the second guide wire 5 causes a shape variation of the flexible end portion 8 making the latter curve-shaped, that is divergent from the longitudinal axis X, so that the flexible end portion 8 can easily engage the side branch 20.

Preferably, the flexible end portion 8, when released from the second guide wire 5, has at least one curved portion.

Even more preferably, the flexible end portion 8, when released from the second guide wire 5, has a number of curved portions adjacent in a longitudinal direction and having different radii of curvature.

In accordance with a specific embodiment of the present invention, said number of curved portions are positioned consecutively to each other.

According to a further variation, said number of curved portions are alternated with one or more substantially rectilinear portions.

Even more preferably, as mentioned above, the flexible end portion 8, when released from the second guide wire 5, has a curved "U" shaped portion, concave towards the distal extremity of the tubular body 3, the curved "U" shaped portion being indicated by reference number 29 (see, for example, FIG. 1).

According to a preferred variation of the present invention, the curved "U" shaped portion 29 is joined to a convex peduncle 30 which forms a counter curvature to the main curvature 29.

Specifically, such conformation of the flexible end portion 8 fitted with the convex peduncle 30 enables the catheter 1 to engage the carotid artery branching off the aorta with particular ease.

According to a further embodiment of the present invention, the second guide wire 5 is of variable flexibility in an axial direction.

Specifically, the second guide wire 5 has a distally increasing flexibility in longitudinal direction of the same guide wire.

According to this embodiment, in fact, when a portion of limited flexibility of the, second guide wire is placed in the inner lumen 7 of the mandrel 6, the former makes it possible to keep the flexible end portion of the mandrel 6 in the first rectilinear configuration.

On the contrary, when a highly flexible portion of the second guide wire 5 is placed in the inner lumen 7 of the mandrel 6, the latter does not keep the flexible end portion 8 of the mandrel 6 directed longitudinally but allows it to reacquire its original shape, that is to return to its secondary configuration.

In addition, since according to this embodiment the second guide wire 5 has variable flexibility in an axial direction, it is possible to obtain other configurations between the two limit configurations (straight and curved) described so far.

This way, in fact, it is advantageously possible to adjust the depth of engagement of the second guide wire 5 inside the flexible end portion 8 so as to obtain a number of different orientations of the latter in relation to the longitudinal axis X, a fact which makes it possible to adapt the catheter 1, and specifically the flexible end portion 8 of the latter, to the various anatomic needs which the operator must deal with during the intravascular procedure.

As mentioned above, the mandrel 6 is preferably movable axially inside the central lumen 4 of the tubular body 3 between a non-use configuration (rest configuration) of the mandrel 6, wherein the flexible end portion 8 is at least partially housed inside the central lumen 4 of the tubular body 3 (as shown for example in FIG. 9), and a use configuration (operative configuration) of the mandrel 6, wherein the flexible end portion 8 protrudes externally from the body opening 3a, as shown, for example, in FIG. 5.

Advantageously, the non-use configuration of the mandrel 6 proves particularly facilitated in the case in which the flexible end portion 8 of the mandrel 6 has a cross-section of a flattened shape, such as elliptical.

In fact, in accordance with such embodiment, the mandrel 6 can be inserted inside the central lumen 4 of the tubular body 3 substantially simultaneously with the first guide wire 11 which comes out of the longitudinal groove 9 and runs parallel to the flexible end portion 8 of the mandrel 6. In the case, however that the flexible end portion 8 does not have a flattened cross-section but a circular cross-section (even of limited diameter), the operator could not move forward or withdraw the two devices (that is the mandrel 6 and the first guide wire 11) simultaneously inside the tubular body 3. The flattened shape however permits the aforesaid simultaneous insertion, the overall external diameter (given by the sum of the lesser diameter of the flexible end portion 8 and of the diameter of the first guide wire 11) proving compatible with the inner diameter of the central lumen 4 of the tubular body 3 (as shown, for example, in FIG. 6b).

As a result, such further embodiment having the flexible end portion 8 with a flattened cross-section, but the same overall external diameter, permits the contemporary advancing of the mandrel 6 (with a possible second guide wire 5 inserted in the inner lumen 7) and the first guide wire 11 inside the tubular body 3 and, therefore, in the body of the patient.

According to a further embodiment of the present invention, the tubular body 3 distally comprises a radially expandable balloon 12.

According to the embodiment shown in FIG. 7, the balloon 12 is joined to the radially external wall 25 of the tubular body 3. In other words, the balloon 12 is joined to the tubular body 4 at the lateral surface facing opposite the central lumen 4.

The balloon 12 identifies, with the radially external wall 25 of the tubular body 3, an expansion chamber 14 of the same balloon. Said expansion chamber 14 is, preferably, substantially toroidal-shaped.

The balloon 12 is suitable for converting from a contracted state (shown, for example, in FIG. 8) to an expanded state (shown, for example, in FIG. 7).

When the balloon 12 is in the contracted state, it defines a translation configuration of the tubular body 3 (and of the catheter 1 as a whole) along the main cavity 2.

In the translation configuration, the balloon is contracted (that is it finds itself in the non expanded state) so as not to create a substantial obstruction in relation to the outer surface of the tubular body 3 and thus allow the tubular body 3 (and the catheter 1 as a whole) to freely translate along the main cavity 2.

When the balloon 12 is in an expanded state, it defines an anchorage configuration of the tubular body 3 to the main cavity 2.

In the anchorage configuration, the surface of the balloon 12 facing the main cavity 2 (or the side branch 20 of the main cavity 2) lies at least partially in abutment against the wall of the blood vessel to prevent the reciprocal movement of the tubular body 3 and of the main cavity 2.

In other words, in the anchorage configuration, the balloon 12 is at least partially expanded and at least a portion of its outer surface is in contact with the inner surface of the blood vessel so as to prevent rotational and/or translational movements between the surfaces in mutual contact. This aspect is particularly important in that the catheter 1 can thus maintain the correct position reached inside the main cavity 2 (or its side branch 20) and intended by the operator, especially at the moment in which further devices are introduced inside the catheter for the completion of the planned operation.

According to the aforesaid embodiment in which the catheter 1 is provided with a balloon 12, the tubular body 3 comprises in addition an inflation lumen 13 suitable for the passage of a fluid, for example a gas or a solution, to perform the expansion and/or the contraction of the same balloon 12.

Specifically, the inflation lumen 13 extends between a proximal portion, operatively connected to one way of the connector, and a distal portion in fluid connection to the balloon 12 in order to perform the two aforesaid configurations of expansion/contraction.

Specifically, the distal portion of the inflation lumen is fluidly connected with the expansion chamber 14.

In the embodiment shown in FIG. 7, the central lumen 4 and the inflation lumen 13 extend in an substantially parallel manner.

According to one possible embodiment of the present invention, the inflation lumen 13 extends longitudinally inside the wall of the tubular body 3, that is the inflation lumen is made in the thickness of the wall of the tubular body 3 (as shown, for example, in FIG. 7a).

According to one particularly advantageous embodiment, the longitudinal axis of the inflation lumen 13 intersects the Z axis(as shown, for example, in FIG. 8a). More in detail, the centre of the inflation lumen, the centre of the inner lumen 7 and the centre of the passage for the guide wire 11 lie on the same axis (the Z axis in FIG. 8a). This way in fact, the catheter 1 maintains a greater symmetry (in relation to the Z axis) and can be directed more easily and correctly in the case of approaching a side branch 20 of the main cavity 2.

Preferably, the tubular body 3 is made at least partially from a thermoplastic material.

Even more preferably, the tubular body 3 is at least partially made from polyether block amide, polyamide, polyimide, polyethylene, polytetrafluoroethylene and/or polyurethane.

According to one embodiment of the present invention, the tubular body 3 comprises a support layer, for example in a metallic or a polymeric material, to improve its dimensional stability.

Preferably, said support element is made by using one or more elements (threads or strands) to form a helical or spiral structure (coil structure) or a more complex structure comprising at least a weft and a warp (braid structure).

Preferably, the metallic support layer is made of stainless steel and/or Nitinol.

According to a further embodiment, the tubular body 3 is made at least partially of a radio-opaque material to allow its identification once inside the main cavity 2.

According to still a further variation, the tubular body 3 comprises at least one marker in radio-opaque material.

Preferably, the mandrel 6 is at least partially made of a polymer material.

Even more preferably, the polymer material of the mandrel is chosen from the group comprising polyether block amide, polyamide, polyimide, polyethylene, polytetrafluoroethylene and polyurethane.

Preferably, the mandrel 6 has variable flexibility in an axial direction and, even more preferably, distally increasing flexibility.

According to one embodiment of the present invention, the flexible end portion 8 of the mandrel 6 is made from thermoplastic material with a surface hardness smaller than that of the tubular body 3 and/or of the proximal portion of the mandrel 6.

Preferably, the flexible end portion 8 of the mandrel 6 has a surface hardness ranging between 10 and 70 Shore D.

Even more preferably, the flexible end portion 8 of the mandrel 6 has a surface hardness ranging between 25 and 55 Shore D.

Preferably, the flexible end portion 8 of the mandrel 6 comprises in addition a support layer, for example metallic or in a polymeric material, to improve its dimensional stability.

Preferably, such metallic support layer is made in stainless steel and/or Nitinol.

According to a further embodiment of the present invention, the flexible end portion 8 of the mandrel 6 is made at least partially in a radio-opaque material to allow its identification after its introduction into the main cavity 2. Alternatively, the flexible end portion 8 of the mandrel 6 comprises at least one marker in radio-opaque material.

A method for conducting and positioning a medical device, for example a guide wire, an angioplasty device, a thromboaspiration device or similar, in a main vessel, such as a blood vessel, comprising a main cavity 2 and at least one side branch or offshoot 20 will now be described.

Such method comprises the step of providing a catheter 1 comprising: a tubular body 3, having a central lumen 4 extending along the tubular body 3 around a longitudinal axis X and presenting a cross-section suitable for the passage of at least one medical device; a mandrel 6, positioned so as to slide along inside the central lumen 4 of the tubular body 3, said mandrel comprising un inner lumen 7, suitable for housing in a sliding manner a second guide wire, distally a flexible end portion 8 and an outer surface 10, facing the tubular body 3, provided at least on a proximal portion with a groove 9 defining, with the inner wall of the tubular body 3, a passage suitable for accommodating in a sliding manner a first guide wire 11.

The method further comprises the following steps of: a) introducing the tubular body 3 into the main cavity 2; b) introducing the mandrel 6 inside the tubular body 3; c) moving the tubular body 3 forward up the main cavity 2 until its distal extremity is positioned at a side branch or offshoot 20; d) moving the mandrel 6 forward until its flexible end portion 8 is positioned at the side branch or offshoot 20.

According to one embodiment, the method according to the present invention further comprises the step of providing a first guide wire 11 (stabilising guide wire) and the step of introducing said first guide wire 11 into the main cavity 2. Furthermore, the method according to the invention comprises in addition the step of moving the first guide wire 11 forward up the main cavity 2 until its distal extremity has gone past the offshoot 20 which must be engaged by the operator (the aforesaid steps are illustrated, for example, in FIG. 10).

The method comprises, in addition, the step of engaging the proximal extremity of the first guide wire 11 in the distal opening 3a of the central lumen 4 of the tubular body 3.

In one possible variation of the method according to the invention, the step of inserting the first guide wire 11 in the central lumen 4 of the tubular body 3 is preceded by a step of introducing the tubular body 3 into the main cavity 2.

Preferably, the step of introducing the first guide wire 11 into the main cavity 2 comprises the step of positioning an introducer, for example in the femoral artery according to methods known of in the art, and of inserting the first guide wire 11 through the aforesaid introducer.

According to one embodiment, the method according to the invention comprises in addition the steps of: a) providing a second guide wire 5; b) introducing said second guide wire 5 into the main cavity 2, and c) moving the second guide wire 5 forward until its distal extremity reaches the offshoot 20 (as shown, for example, in FIG. 10).

The method comprises, in addition, the step of engaging the proximal extremity of the second guide wire 5 in the inner lumen 7 of the mandrel 6 through the tip opening 8a of the said mandrel.

In one variation, the method according to the present invention foresees that the step of inserting the second guide wire 5 in the mandrel 6 is performed before introducing the mandrel 6 into the main cavity 2.

Advantageously, the second guide wire 5 is suitable for performing shape changes in the flexible end portion 8 of the mandrel 6.

Preferably, the step of introducing the second guide wire 5 into the main cavity 2 comprises the step of inserting the second guide wire 5 through an introducer.

The method according to the invention comprises, in addition, the step of inserting the distal extremity of the mandrel 6 into the proximal opening of the central lumen 4 of the tubular body 3.

In one possible variation of the method of the invention, the step of inserting the mandrel 6 into the tubular body 3 is performed before introducing the mandrel 6 into the main cavity 2.

In this possible variation of the method according to the invention, the steps of moving forward the tubular body 3 and the mandrel 6 in the main cavity 2 are performed at least partially simultaneously.

Once the catheter 1 is positioned inside the main cavity 2 near the side branch 20 it proves particularly advantageous to be suitable for stabilising the catheter 1 in the main cavity 2.

In one variation of the method according to the invention, the method therefore comprises the step of stabilising the tubular body 3 inside the main cavity 2.

The step of stabilising the tubular body 3 consists of making the first guide wire 11 advance so that it comes out of the passage defined by the outer surface 10 and by the inner wall of the tubular body 3, and extends in a distal direction inside the main cavity 2.

The method and the catheter according to the present invention are particularly suitable in the case in which the main vessel has an arched configuration from which at least one lateral duct branches off (offshoot), preferably directed in an substantially orthogonal direction to the main vessel. More specifically, the method and the catheter according to the present invention are particularly suitable in the case in which the main cavity 2 is the aortic arch.

The steps of the method according to the invention have been shown with reference to the aortic arch (see specifically FIGS. 10 to 15). However, such figures are provided merely as an example and the method, as well as the catheter, according to the present invention may be applied to any main cavity 2 comprising a side branch 20.

Advantageously, the disposition of the first guide wire 11 in an extended tract of the aortic arch makes it possible to stabilise the catheter 1 and to make the engagement of the same in the side branch 20 easier to reproduce.

Once the catheter 1 has been stabilised, it must be correctly orientated in relation to the entrance of the side branch 20.

Specifically, once the flexible end portion 8 of the mandrel 6 is near the bifurcation area, the flexible end portion 8 must be oriented so that the tip opening 8a looks onto the opening of the side branch 20. Such operation proves particularly simplified in the case in which the flexible end portion 8 is made, at least partially, from a radio-opaque material.

The method according to the invention also comprises, therefore the step of orienting the flexible end portion 8 of the mandrel 6.

As described above, the translation of the second guide wire 5 in relation to the flexible end portion 8 of the mandrel 6 allows to control the flexible end portion 8 and, specifically, to pass from a first rectilinear configuration, wherein it extends substantially along the longitudinal axis X, to at least a second curved configuration, wherein it is curved so as to engage the side branch.

The step of orienting the flexible end portion 8 comprises the step of drawing back the second guide wire 5 so as to allow the flexible end portion 8, preferably pre-curved, to return to its original second configuration.

Figure 11:
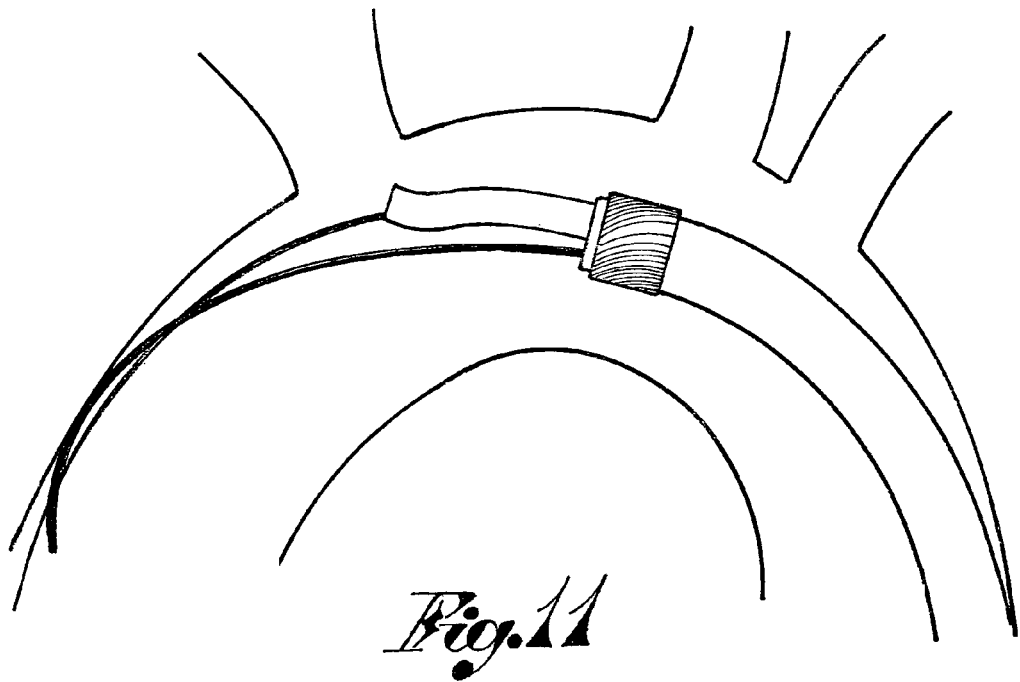

Specifically, the step of drawing back the second guide wire 5 comprises the step of taking it out, that is to say, moving it proximally, completely from the flexible end portion 8 or drawing it back until a more flexible portion of said second guide wire 5 is brought to the flexible end portion 8 (see FIG. 11).

The step of orienting the flexible end portion 8 of the mandrel 6 comprises, in addition, the step of turning the catheter assembly using the first guide wire 11 so as to position the tip opening 8a of the mandrel 6 substantially in front of the entrance of the side branch 20.

As mentioned above, this operation is simplified by the fact that, according to a preferred embodiment of the catheter according to the invention, the axis of the longitudinal groove 9, and therefore of the first guide wire 11, is aligned, in relation to the longitudinal axis X of the catheter 1, with the axis of the inner lumen 7 of the mandrel 6 and, consequently with the second guide wire 5.

According to an alternative variation, the step of orienting the flexible end portion 8 of the mandrel 6 comprises the step of turning the mandrel 6 alone so as to position the tip opening 8a exactly in front of the entrance of the side branch 20 (side branch).

Advantageously, the method according to the invention comprises, in addition, the step of moving forward the mandrel 6 until it goes in abutment against an inner wall of the side branch 20 (see, for example, FIG. 12).

In fact, once the catheter 1 has been correctly stabilised and directed, the operator may advance the mandrel 6 in a distal direction so that the curvature of its flexible end portion 8 hits against the inner wall 30 of the side branch 20.

This way, when the operator pushes the second guide wire 5 in a distal direction towards the inside, of the side branch 20 of the bifurcation, the mandrel 6 does not risk to return into the main cavity 2, thus making the entire catheter 1 lose the correct orientation.

This situation is avoided thanks to the support supplied by the arch formed by the first guide wire 11, also called "stabilisation wire", which sustains the entire catheter 1 and supports it with a reaction force in a distal direction, and thanks to the mandrel 6 which lies and is anchored inside the side branch.

The method according to the invention comprises, in addition, the step of moving forward the second guide wire 5 inside the side branch 20 of the bifurcation.

Figure 13:
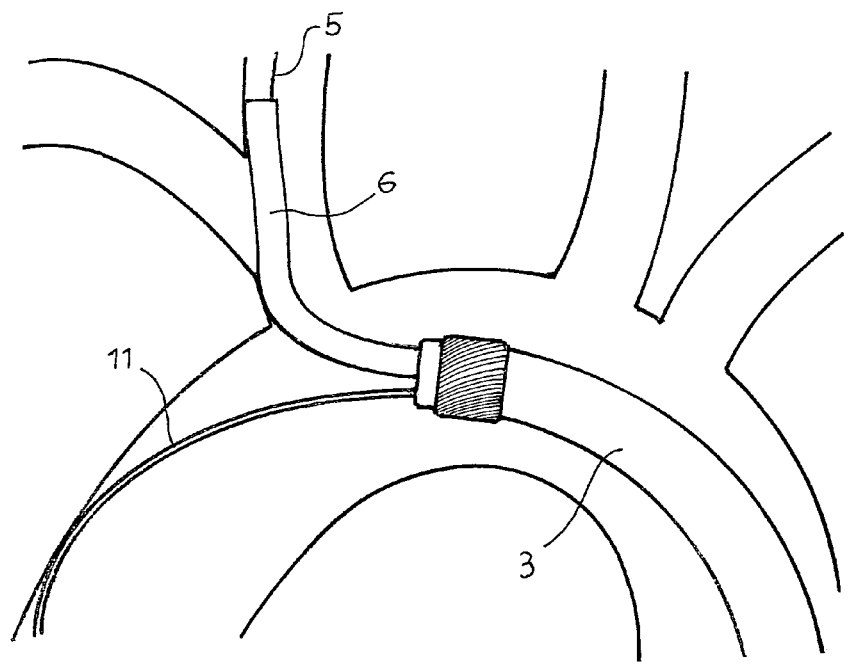

To perform this step, the flexible end portion 8 of the mandrel 6 is again commanded to bring itself into a semi-rectilinear configuration to be introduced into the side branch, for example making the second guide wire 5 advance in relation to the mandrel 6 (see, for example, FIG. 13).

The advancement of the second guide wire 5 is performed by applying, in the proximal area, a thrust force in a distal direction. At the same time in the bifurcation area, a local reaction force, proportional to the distal thrust force impressed, is exerted on the catheter assembly and, specifically, on the first guide wire 11. Such reaction force insists on the arch formed by the first guide wire 11 (positioned in the aortic arch), which reacts to the point load by distributing it along all the length of the arch with the advantageous and desired effect of stabilising the entire structure. Such technical effect is extremely advantageous in that it makes it possible, or at least facilitates, the advancement of the second guide wire 5 (which is more flexible than the first guide wire 11) towards the side branch.

As shown in FIG. 13, in such step of the procedure the flexible end portion 8 is inserted in the side branch 20, while the first stabilisation guide wire 11 is positioned in the main cavity 2, that is in the aortic tract. To enable the subsequent advancement of the tubular body 3 in the side branch 20 (as shown, for example, in FIG. 14), the operator draws back the first guide wire 11 to the inside of the central lumen 4 of the tubular body 3 of the catheter 1.

As a result, advantageously the method according to the present invention comprises the step of drawing back the first guide wire 11 to the inside of the central lumen 4 of the tubular body 3.

In the case in which to reach the main vessel being subjected to intravascular operation it should be necessary to repeat the operations of intercepting a side branch, as described above, twice or more, the first guide wire 11 is drawn back to the inside of the tubular body 3.

Figure 14:
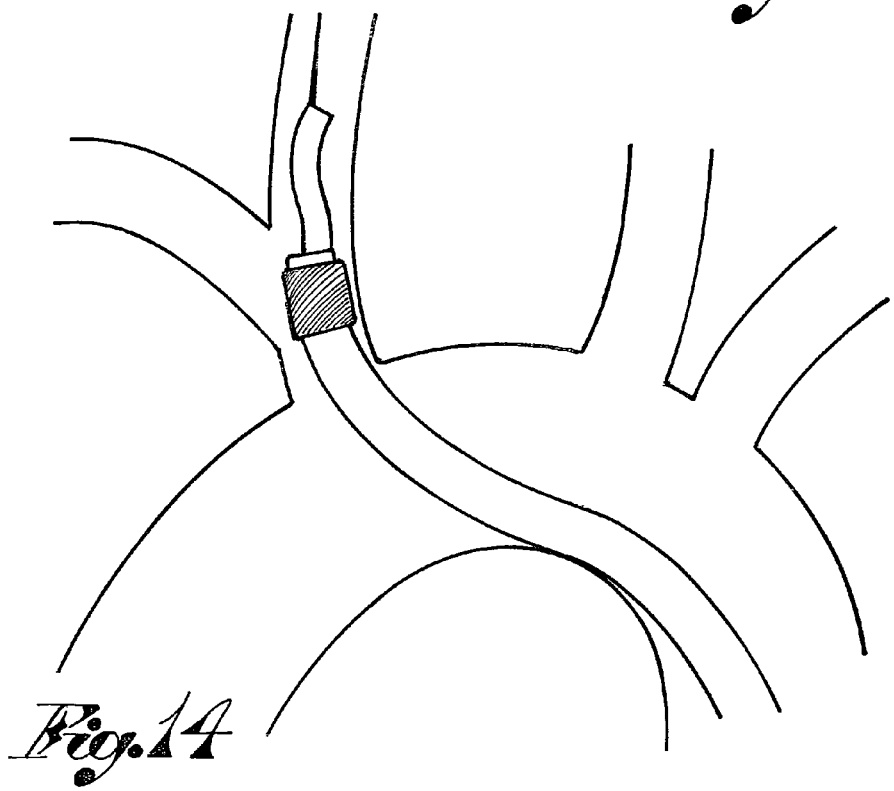

In this case, the entire catheter 1 (with mandrel 6 and first guide wire 11 contained in the central lumen 4 of the tubular body 3) is moved forward along the second guide wire 5 inside the side branch 20 (see, for example, FIG. 14).

The method according to the invention comprises therefore, the step of moving forward the catheter 1 inside the side branch 20.

If, on the contrary, the main vessel to be subjected to the intravascular operation has been reached or it is no longer necessary to repeat the operations of intercepting a side branch as described above, the first guide wire 11 and the mandrel 6 are withdrawn and extracted from the tubular body 3 and the latter is moved forward alone along the second guide wire 5, in the side branch 20.

The method according to the invention comprises, therefore, the step of forward the tubular body 3 in the side branch 20.

Once the main vessel being subjected to the intravascular operation has been reached as described above, the first guide wire 11 is retracted and extracted with the mandrel 6.

Consequently, the method according to the invention comprises the step of extracting the mandrel 6 and/or the first guide wire 11 from the main cavity 2.

The method comprises, in addition, the step of extracting the first guide wire 11 from the body of the patient.

Advantageously, the steps of extracting the mandrel 6 and the first guide wire 11 are performed at least partially simultaneously.

At this point of the operation procedure, advantageously, the method according to the invention comprises the step of engaging a further device 28 in a slidable manner in the central lumen 4 of the tubular body 3 to complete the intravascular operation planned by the operator. Such further device may be, for example, an angioplasty device, a device for the mechanical recovery of a thrombus (as schematically shown in FIG. 15) or a device for the aspiration of a thrombus (as schematically shown in FIG. 16).

According to a further embodiment, the method according to the present invention comprises the step of radially expanding a balloon 12 provided distally on the tubular body 3, between a translation configuration of the tubular body 3 along the vessel and an anchorage configuration of the tubular body 3 to such vessel, in which the intravascular operation must be conducted (see, for example, FIG. 15).

The step of radially expanding the balloon 12 comprises the step of introducing an inflating fluid inside the balloon through the inflation lumen 13.

Once the tubular body 3 has been firmly anchored in the main cavity 2 or in the side branch 20 following the positioning and inflating of the balloon 12 (as shown, for example, in FIG. 15), in accordance with a particular embodiment of the present invention, said tubular body 3 may be used as an aspiration device.

In such case in fact, once the mandrel 6, the first guide wire 11 and second guide wire 5 have been extracted, the balloon 12 allows blocking of the blood flow and prevents any fragments (such as stenotic or thrombic fragments) from being transported along the main vessel being treated.

In addition, the central lumen 4 of the tubular body 3 being most ample (being designed in fact to accommodate at least one other medical device) and having no lateral holes (which would have a particularly negative dispersive effect) proves particularly suitable for performing an aspiration operation, as shown schematically in FIG. 17.

As a result, the catheter which the present invention relates to makes the engagement of the said catheter in bifurcations where the side branch has an accentuated inclination in relation to the extension of the main vessel, particularly easy and rapid.

This way, the risks for the patient connected with the intravascular operation are considerably reduced in that the operator takes a shorter time to complete the desired operation.

In addition, in accordance with the present invention a single device allows to perform, in succession, the positioning of a guide wire, the surpassing of a bifurcation, the anchorage of a tubular body (or guide catheter) and an eventual aspiration operation.

In other words, the multipurpose device according to the present invention enables an operator to use a single medical device to position and anchor a guide catheter (tubular body) in a desired position of a blood vessel.

Advantageously, the flexible end portion of said guide catheter is convertible between at least two configurations to allow the introduction of the catheter in the relative main vessel and its correct engagement in one or more branches of the latter.

Advantageously, the tubular body presents a cross-section suitable for the passage of medical devices inside it, so as to accommodate them in a slidable manner in the central lumen of the tubular body itself.

Advantageously, the presence of a distal balloon makes it possible to firmly anchor the catheter to the main vessel or to one of its side branches, so as to avoid a relative movement between the tubular body and the wall of the said vessel.

This way it is furthermore possible to replace a device in use with another device, by simply introducing the latter from the proximal extremity of the tubular body, without having to search once again for the correct path to reach the operation area.

All this means time saving (thanks to the reduction of the number of attempts to intercept the side branches and of the number of medical devices to be used) which is an extremely critical factor, especially in the case of operations in the carotid area.

Advantageously, the surface of the mandrel facing the first guide wire is shaped so as to act as a guide of the latter.

In fact, this way the first guide wire and the second guide wire are positioned inside the catheter 1 in a substantially parallel manner so as to prevent them from dangerously crossing over during the operation.

In other words, the first guide wire and the second guide wire are confined in special, independent movement seats, separated from each other.

Thanks to the absence of lateral openings made in the tubular body, the latter can advantageously be used to perform aspiration operations, after removing the first, second guide wire and/or mandrel.

A person skilled in the art may make modifications, adaptations and substitutions to the embodiments of the catheter, the assembly and the method described above, so as to satisfy contingent requirements, while remaining within the scope of protection as defined by the appended claims.

Each of the features described as belonging to a possible embodiment, may be realised independently of the other embodiments shown.

The invention claimed is:

1. A catheter assembly suitable for conducting and positioning a medical device in an organic vessel having a main cavity and at least one side branch said catheter assembly comprising:
    first and second guide wires; and
    a catheter comprising
    a tubular body, having a central lumen extending along said tubular body around a longitudinal axis (X), said central lumen having a cross-section such as to allow the passage of at least one medical device, wherein the tubular body distally comprises a radially expandable balloon that is configurable between a non-expanded state that defines a translation configuration of the tubular body and an expanded state that defines an anchorage configuration of the tubular body and wherein the tubular body comprises an inflation lumen for the introduction of a fluid suitable for causing the expansion and/or contraction of the balloon; and
    a mandrel slidably positioned inside said central lumen, said mandrel including
        a flexible distal end portion having a proximal extremity and a distal extremity and having one of a substantially elliptical, oval or semicircular cross-section,
        a proximal portion having an outer surface, facing the tubular body with a longitudinal groove, wherein said longitudinal groove defines with an inner wall of the tubular body a passage suitable for receiving said first guide wire in a sliding manner and wherein said longitudinal groove ends at said proximal extremity of said flexible distal end portion with a distal opening in the direction of the longitudinal axis (X), and
        an inner lumen suitable for receiving said second guide wire in a sliding manner that extends within said proximal portion and said flexible distal end portion, wherein a tip opening for accessing said inner lumen is disposed at said distal extremity of said flexible distal end portion.

2. The catheter assembly according to claim 1, wherein the longitudinal groove and the inner lumen have respective longitudinal axes parallel to the longitudinal axis (X).

3. The catheter assembly according to claim 2, wherein said longitudinal axes intersect a first axis (Z) passing substantially through the centre of the inner lumen and substantially through the centre of the longitudinal groove, on opposite sides to a second axis (Y), orthogonal to said first axis (Z) and which separates the inner lumen from the longitudinal groove.

4. The catheter assembly according to claim 3, wherein the flexible distal end portion is movable between a first configuration, wherein it extends substantially along the longitudinal axis (X), and at least a second configuration, wherein it is curved.

5. The catheter assembly according to claim 4, wherein the curvature of the flexible distal end portion is around an axis parallel to said second axis (Y).

6. The catheter assembly according to claim 1, wherein the flexible distal end portion is pre-shaped so as to curve in a direction opposite of the longitudinal groove.

7. The catheter assembly according to claim 1, wherein the flexible distal end portion has a plurality of curved portions, adjacent in a longitudinal direction, having different radii of curvature.

8. The catheter assembly according to claim 1, wherein the flexible distal end portion has a curved U-shaped section, concave towards a distal extremity of the tubular body.

9. The catheter assembly according to claim 8, wherein the curved U-shaped section is joined to a convex peduncle.

10. The catheter assembly according to claim 1, further comprising: an externally tapered portion in distal direction.

11. The catheter assembly according to claim 1, wherein the mandrel has an axially variable flexibility.

12. The catheter assembly according to claim 11, wherein the mandrel has a distally increasing flexibility.

13. The catheter assembly according to claim 1, wherein a distal extremity of the tubular body comprises an opening for accessing the central lumen, and wherein the mandrel is axially movable in the central lumen between a non-use configuration of the mandrel, wherein the flexible distal end portion is at least partially housed in the central lumen, and a use configuration of the mandrel, wherein the flexible distal end portion protrudes from the opening.

14. The catheter assembly according to dam 1, wherein the inflation lumen extends longitudinally inside a wall of the tubular body.

15. The catheter assembly according to claim 1, wherein the inflation lumen has a longitudinal axis which intersects a first axis (Z) passing substantially through the centre of the inner lumen and substantially through the centre of the longitudinal groove.

16. The catheter assembly according to claim 1, further comprising:
    said first guide wire disposed within said passage, in relation to which the tubular body is axially movable and suitable for turning said tubular body around an axis substantially parallel to the longitudinal axis (X); and
    said second guide wire disposed within said inner lumen suitable for causing shape changes of the flexible distal end portion of the mandrel.

17. The catheter assembly according to claim 16, wherein said second guide wire is movable and/or slidable in relation to the flexible distal end portion between a first configuration, wherein the flexible distal end portion extends substantially along the longitudinal axis (X), and at least a second configuration, wherein the flexible distal end portion is curved.

18. The catheter assembly of claim 16, wherein a portion of said first guide wire that extends from the distal opening of said longitudinal groove of the mandrel proximal portion extends adjacent to and parallel with said flexible distal end portion of the mandrel when said flexible distal end portion is housed in the central lumen of the tubular body in a non-use configuration.

19. The catheter assembly according to claim 1, further comprising:
    a medical device engageable in a slidable manner in the central lumen of the tubular body of the catheter.

* * * * *